United States Patent
Mertens

(10) Patent No.: US 9,850,454 B2
(45) Date of Patent: *Dec. 26, 2017

(54) THICKENING POLYMER

(75) Inventor: Sascha Mertens, Reinbek (DE)

(73) Assignee: BEIERSDORF AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/126,021

(22) PCT Filed: Jun. 15, 2012

(86) PCT No.: PCT/EP2012/061507
§ 371 (c)(1),
(2), (4) Date: Feb. 4, 2014

(87) PCT Pub. No.: WO2013/017328
PCT Pub. Date: Feb. 7, 2013

(65) Prior Publication Data
US 2014/0336101 A1    Nov. 13, 2014

(30) Foreign Application Priority Data

Jun. 27, 2011 (DE) ........................ 10 2011 078 087

(51) Int. Cl.
| | | |
|---|---|---|
| *C11D 3/37* | (2006.01) | |
| *C08F 220/18* | (2006.01) | |
| *A61Q 19/10* | (2006.01) | |
| *C08F 220/26* | (2006.01) | |
| *C08F 2/26* | (2006.01) | |
| *A61K 8/81* | (2006.01) | |

(52) U.S. Cl.
CPC .......... *C11D 3/3765* (2013.01); *A61K 8/8152* (2013.01); *A61Q 19/10* (2013.01); *C08F 2/26* (2013.01); *C08F 220/18* (2013.01); *C08F 220/26* (2013.01); *A61K 2800/262* (2013.01); *A61K 2800/48* (2013.01); *A61K 2800/548* (2013.01); *C08F 2220/1808* (2013.01)

(58) Field of Classification Search
CPC ....... C11D 3/37; C11D 3/3707; C11D 3/3757; C08F 220/18
USPC ..... 510/476; 526/318, 318.43; 524/558, 560
See application file for complete search history.

(56) References Cited

U.S. PATENT DOCUMENTS

| | | |
|---|---|---|
| 6,242,531 B1 | 6/2001 | Craun et al. |
| 6,635,702 B1 | 10/2003 | Schmucker-Castner et al. |
| 6,897,253 B2 | 5/2005 | Schmucker-Castner et al. |
| 7,153,496 B2 | 12/2006 | Tamareselvy et al. |
| 7,288,616 B2 | 10/2007 | Tamareselvy et al. |
| 7,649,047 B2 | 1/2010 | Tamareselvy et al. |
| 2002/0193548 A1 | 12/2002 | Throne et al. |
| 2003/0202953 A1 | 10/2003 | Tamareselvy et al. |
| 2003/0207988 A1* | 11/2003 | Tamareselvy et al. ....... 524/800 |
| 2004/0087668 A1 | 5/2004 | Schmucker-Castner et al. |
| 2004/0143074 A1 | 7/2004 | Throne et al. |
| 2005/0032998 A1 | 2/2005 | Morschhaeuser et al. |
| 2005/0158268 A1 | 7/2005 | Schmucker-Castner et al. |
| 2006/0251600 A1 | 11/2006 | Tamareselvy et al. |
| 2007/0161524 A1 | 7/2007 | Counradi et al. |
| 2007/0293617 A1 | 12/2007 | Riegel et al. |
| 2008/0045646 A1 | 2/2008 | Tamareselvy et al. |
| 2013/0203866 A1 | 8/2013 | Aleksandrovic-Bondzic et al. |

FOREIGN PATENT DOCUMENTS

| | | |
|---|---|---|
| DE | 10059830 A1 | 6/2002 |
| DE | 102010022063 A1 | 12/2011 |
| EP | 1266909 A2 | 12/2002 |
| WO | 03061615 A1 | 7/2003 |
| WO | 03062288 A1 | 7/2003 |
| WO | 2005030163 A1 | 4/2005 |
| WO | 2006058683 A2 | 6/2006 |
| WO | 2007090759 A1 | 8/2007 |
| WO | 2011151091 A1 | 12/2011 |

* cited by examiner

*Primary Examiner* — Brian P Mruk
(74) *Attorney, Agent, or Firm* — Abel Law Group, LLP

(57) ABSTRACT

Polymer obtainable by radical emulsion polymerization of (A) at least one acidic vinyl monomer or salt thereof; (B) at least one nonionic vinyl monomer, particularly preferably a hydrophobic nonionic vinyl monomer; (C) at least one monomer containing an unsaturated end group and a polyoxyalkylene part; (D) at least one crosslinking monomer; and (E) optionally, a protective colloid, characterized in that the polymerization is controlled such that (F) the gel effect occurs, at least at times, achieved by adding monomers of type (A), (B), and (C) (dosing time) during 120 minutes; and such that (G) the crosslinking monomer (D) is added, at the very earliest, 10 minutes after the first addition of the monomers (A), (B), and (C).

20 Claims, No Drawings

THICKENING POLYMER

BACKGROUND OF THE INVENTION

1. Field of the Invention

The invention relates to a new type of thickening polymer with special properties which is free from associative monomers and its chain contains no such associative monomers, respectively. Unless stated otherwise, all of the quantitative data are percentages by mass based on the total mass of the preparation.

Within the context of the present document, associative monomers are monomers of the U-S-L type, where U contains an ethylenically unsaturated group such as methacrylate, acrylate, allyl or vinyl groups, S is a spacer made of a polyoxyalkylene chain having 2 to 300 alkyleneoxy units such as polyethylene glycol, polypropylene glycol or polybutylene glycol, and L is a hydrophobic group such as an alkyl and/or aryl group, which has at least 4, preferably at least 8, carbon atoms, for example a lauryl group.

Within the context of the present document, tan δ value means the quotient of the loss modulus and the storage modulus, in each case measured at 40° C. The measurement instrument used is unimportant here. The values given in this document were determined using the Malvern Gemini HR nano. In general, thickening polymers serve to thicken water or water-containing preparations. In this connection, the water causes the polymers to swell to gels so as to influence viscosity and flow behavior.

2. Discussion of Background Information

Thickening polymers are of importance for the production of body cleaning compositions, creams, cleaners, finishes, printing inks, paints, emulsion paints and other coating materials, adhesives, paper, foods and so on.

EP 1465932 B1 discloses alkali-swellable and alkali-soluble associative multipurpose polymers which are the polymerization product of a monomer mixture of (a) at least one acid-containing vinyl monomer, (b) at least one nonionic vinyl monomer, (c) a first associative monomer, which has a first hydrophobic end group, (d) a second associative monomer with a second hydrophobic end group, a semi-hydrophobic monomer and from a combination thereof and optionally (e) one or more crosslinking monomers or chain transfer agents.

Such polymers are prepared by emulsion polymerization. Here, firstly the monomer mixture is emulsified or suspended with a surfactant in water in the form of micelles. The actual reactor is charged with the initiator in aqueous solution or suspension, and the monomer suspension is slowly added. The rate of monomer addition is controlled such that it does not result in a considerable increase in the reaction temperature as a result of the Trommsdorff effect (gel effect). The gel effect arises upon too great an increase in the conversion and leads to the polymerization rate increasing as a result of the diffusion of the polymer radicals being hindered, and the rate of the polymerization itself increases. Attempts are made to prevent this for reasons of safety and in order to obtain a narrow molar mass distribution. If the gel effect arises, then a bimodal molar mass distribution is obtained.

Further prior art can be found in EP 1272159, WO03062288, WO03061615, WO2007090759, U.S. Pat. No. 6,242,531.

Thickening polymers are desirable with which it is possible to thicken aqueous preparations in such a way that gels that are as clear as possible are formed. In particular it was desirable to provide body cleansing products with turbidity values below 20 NTU.

Thickening polymers with which, in aqueous solution, the lowest possible tan δ values (in words: tangent delta) can be achieved are also desirable. In particular, it was desirable to provide body cleansing products with tan δ values below 0.5 (in words: tangent delta).

Thickening polymers with a significantly extended storage stability are likewise desirable. In particular it was desirable to provide thickened body cleansing products with good storage stability at temperatures above 40° C., particularly those which do not turn cloudy.

Likewise desirable are thickening polymers with which transparent cosmetic cleansing products can be produced which, when spread virtually evenly, contain visible particles or bubbles. These should remain virtually unchanged in their position even after prolonged standing times at various temperatures (0°-40° C.) and should also be suitable for preparations with pH values below 6.4 and in so doing ensure a viscosity appropriate for use and a viscoelasticity necessary for stabilizing the particles. This is desirable so that the preservatives benzoic acid and/or salicylic acid and salts thereof can be used. These organic acids develop an adequate antimicrobial effect, but only in a pH range <6.4; this means that hitherto formulations of the desired type had to be stabilized with less preferred preservatives.

Likewise desirable are thickening polymers which are compatible with anionic (up to 10%), amphoteric (up to 10%) and nonionic surfactants with total surfactant use concentrations up to 20%.

Likewise desirable are thickening polymers which are compatible with cationic polymers (up to 0.5%) and insensitive towards electrolytes (0.1-4%, preferably up to 3%, particularly preferably up to 2%).

Likewise desirable are thickening polymers which have no negative effect on foam formation and sensorics, are simple and stable to store and can be incorporated easily.

The prior art lacked thickening polymers which permit the preparation of clear gels with simultaneously low tan δ values (in words: tangent delta), where, if possible, at the same time a gel having pH values below 6.4, a yield point and a compatibility with anionic (up to 10%), amphoteric (up to 10%) and nonionic surfactants with total surfactant use concentrations up to 20% and an insensitivity towards electrolytes (0.1-4%) is achieved.

SUMMARY OF THE INVENTION

In a manner that is surprising and could not have been foreseen by the person skilled in the art, it has now been found that a polymer obtainable by radical emulsion polymerization of (A) at least one acidic vinyl monomer or salt thereof, (B) at least one nonionic vinyl monomer, particularly preferably a hydrophobic nonionic vinyl monomer, (C) at least one monomer containing an unsaturated end group and a polyoxyalkylene moiety, (D) at least one crosslinking monomer, (E) optionally a protective colloid, characterized in that the polymerization is controlled such that (F) at least at times the gel effect arises, achieved by adding the monomers (A), (B) and (C) (dosing time) over 120 minutes, preferably 60 minutes, particularly preferably 40 minutes, very particularly preferably 30 minutes, and (G) starting the addition of the crosslinking monomer (D) at the earliest 10 minutes, preferably at the earliest 15 minutes, after the first addition of the monomers (A), (B) and (C), overcomes the deficiencies of the prior art. During such a polymerization while exploiting the Trommsdorff effect, i.e. with constant addition of the monomers and simultaneously high rate of addition of the monomers, a monomer excess is formed which leads to an auto-acceleration of the polymerization (Trommsdorff effect). The result is an increase in molecular weights with a simultaneously advantageous morphology of the polymers. In this connection, it is advantageous if the temperature during the polymerization is kept between 70 and 90° C., preferably 80 and 90° C. It is further advantageous if the initiator is added both before the start of the dosing time and also after the addition of the crosslinking monomer. In this connection, it is particularly preferred if (H) associative monomers are missing or have at most a concentration of 15% by weight, preferably 10% by weight, particularly preferably 5% by weight, very particularly preferably 2.5% by weight, very extraordinarily preferably 1% by weight, very particularly extraordinarily preferably 0.1% by weight. It is particularly preferred if the acidic vinyl monomer (A) is selected from vinyl monomers with carboxyl groups, particularly preferably acrylic acid or methacrylic acid or alkali metal, alkaline earth metal, ammonium or alkylammonium salts thereof. It is particularly preferred if the nonionic vinyl monomer (B) is selected from the group of the C1-C22-alkyl acrylates and of the C1-C22-alkyl methacrylates, and mixtures thereof. As a result, good flow properties and consequently an advantageous rheological profile are achieved. It is particularly preferred if the monomer (C) containing an unsaturated end group and a polyoxyalkylene moiety is selected from vinylpolyalkylene glycols or polymerizable surfactants or mixtures thereof, is particularly preferably selected from vinylpolyalkylene glycols or polymerizable surfactants or mixtures thereof, is preferably selected from ethoxylated and propoxylated 1,4-butanediol vinyl ethers having 30 ethyleneoxy and propyleneoxy units, allylpolyethylene glycol ethers having 30 ethyleneoxy units, allylpolyethylene glycol ethers having 20 ethyleneoxy units, vinylpolyethylene glycol ethers having 20 ethyleneoxy units, $CH_2$=$CHCH_2O[(CH_2CH_2O)_n(CH_2(CH_3)CHO)]_mCH_3$ where m+n=5 to 100 and n/m=1, polyalkylene glycol allyl butyl ethers having 25 ethyleneoxy and 8 propyleneoxy units, very particular preference being given to using Emulsogen 8307 (EO/PO 30 1,4-butanediol vinyl ether (EO/PO 30 mol), Clariant), Emulsogen RAL307 (allylpolyalkylene glycol ether (EO 30 mol), Clariant), Polyglycol A11/1800 (allylpolyalkylene glycol ether) (EO 20 mol, PO 20 mol), Clariant), Polyglycol R1100 (vinylpolyalkylene glycol ether (EO 20 mol), Clariant), Pluriol A111R (allyl alcohol alkoxylate, BASF) or Polyglycol AB25-8 (polyalkylene glycol allyl butyl ether (EO 25 mol, PO 8 mol), Clariant). Polyglycol A11/1800 has proven particularly useful, and is therefore extraordinarily preferred. It is particularly preferred if the crosslinking monomer (D) is selected from polyol (meth)acrylates with at least two (meth)acrylate groups and the mixed esters of polyols with acrylic acid and/or methacrylic acid. It is further particularly preferred if the monomers (A) are present in contents of from 10 to 75%, preferably 20 to 60%, particularly preferably 28 to 52%, very particularly preferably 32 to 52%, (B) are present in contents of from 10 to 90%, preferably 30 to 80%, particularly preferably 40 to 62%, very particularly preferably 40 to 60%, (C) are present in contents of from 0.5 to 40%, preferably 1 to 10%, particularly preferably 2 to 6%, (D) are present in contents of up to 1%, preferably 0.05 to 0.5%, particularly preferably 0.1 to 0.3%. It is very particularly preferred if the monomers (A):(B) are present in mass ratios of 1:2.2 to 1.5:1, preferably 1:1.6 to 1.3:1. It is very particularly preferred if the addition of the crosslinking monomer starts at the earliest after 10 minutes, particularly preferably after 15 minutes, and either ends immediately or lasts until the end of the dosing time of the monomers. It is very particularly preferred if the polymer is selected from examples 7, 8 and 12. The invention also encompasses a thickened preparation comprising a polymer as claimed in one of the preceding claims. It is particularly preferred if the use concentration of the polymer for thickening aqueous, preferably surfactant-containing aqueous, preparations is 0.5 to 5%, preferably 1 to 4%, particularly preferably up to 3%. As a result, the preparation becomes transparent at pH values <6.5 and has a viscosity of at least 2000 mPa·s, which enables added suspended substances not to settle out, where the suspended substances may be beads, pigments or air bubbles. It is particularly preferred if the preparations according to the invention are a health product, cleaning product, household product, shower gel, paint, inks, dispersant, anti-settling agent, concrete and cement additives, coatings, medicinal product, cosmetic product or dermatological product. The invention also encompasses the use of a polymer according to the invention as thickener, emulsifier, dispersant or consistency regulator.

The preparations—if they are gel-like preparations with a yield point—are advantageously configured such that they have a yield point of 0.5-20 Pa, preferably 1-6 Pa.

The yield point is considered to be the critical shear stress of the flow curve. According to the invention, it can be determined as follows:

The flow curve is measured on a shear-stress-controlled rheometer at 25° C.±1° C. with 20 mm plate/plate geometry with a gap between 0.8 mm and 1.2 mm, with charging being carried out in a structure-preserving manner. A suitable constant shear stress time ramp is predefined and before the test a corresponding structure recovery time is observed and the critical shear stress is given as the maximum of the flow curve.

The preparations are advantageously configured such that they have a tan δ (in words: tangent delta) of 0.05-0.6, preferably 0.1-0.5.

According to the invention, tan δ (in words: tangent delta) is understood as meaning the quotient from the loss modulus and the storage modulus. The tan δ is determined as follows:

Loss and storage moduli are measured by a dynamic frequency test run with a shear-stress-controlled rheometer at 40° C.±1° C. with 20 mm plate/plate geometry with a gap between 0.8 mm and 1.2 mm, charging being carried out in a structure-preserving manner. The frequency test is carried out in accordance with the prior art with an appropriate structure recovery time before the test, and the tan δ (in words: tangent delta) in the frequency range between 0.05 rad/s and 3.0 rad/s is indicated, preferably between 0.08 rad/s and 1.0 rad/s.

The preparations are advantageously configured such that, at pH <6.2, they have a turbidity value of NTU (Nephelometric Turbidity Unit) <20. The turbidity value is measured using a turbidity measuring device, with distilled water having a value of NTU=0 serving as standard. It is also in accordance with the invention if not water, but other polar liquids are thickened by polymers according to the invention. In particular, alcohols, glycols, polyols, amines and organic acids such as, for example, acrylic acid, and aqueous solutions thereof can be thickened. The use of polymers according to the invention as emulsifier is also in accordance with the invention. In this way, creams and lotions can be provided.

The polymers are also suitable as dispersants and antisettling agents.

DETAILED DESCRIPTION OF THE INVENTION

Examples

Synthesis of the Copolymers

The examples below are intended to illustrate the present invention without limiting it. The preparation of the examples takes place in accordance with the method described below, the type and amounts of the monomers used in each case as starting components being summarized in Table 2. Parts and percentages refer to the weight.

Example 1

Monomer Phase
Methacrylic acid 37.000 parts
Ethyl acrylate 57.400 parts
Polyglycol A11/1800 5.400 parts
Crosslinker Phase
Trimethylolpropane triacrylate 0.300 parts
Water Phase
Water 33.060 parts
Sodium lauryl sulfate 0.984 parts
Reaction Vessel
Water 173.146 parts
Sodium lauryl sulfate 0.300 parts Initiator Phase A
Water 1.911 parts
Ammonium persulfate 0.069 parts
Initiator Phase B
Water 2.909 parts
Ammonium persulfate 0.021 parts The reaction vessel, which is equipped with stirrer, reflux condenser, nitrogen feed, dosing device and internal thermometer, is charged with 173.146 parts of water and 0.300 parts of sodium lauryl sulfate. The mixture is heated to 82° C. with stirring and under a nitrogen atmosphere. The monomer mixture is prepared in a second stirred vessel which is equipped with stirrer and nitrogen feed. For this purpose, the monomer phase with 37.000 parts of methacrylic acid, 57.400 parts of ethyl acrylate and 5.400 parts of polyglycol A11/1800 is introduced, and into this is mixed the water phase with 33.060 parts water and 0.984 parts sodium lauryl sulfate with stirring and under a nitrogen atmosphere.

As soon as a temperature of 82° C. has been reached in the reaction vessel, an initiator phase A, consisting of 0.069 parts ammonium persulfate and 1.911 parts water, is added and the monomer mixture is metered in uniformly at 85-88° C. over the course of 30 minutes. 20 minutes after the start of the monomer dosing, the crosslinker phase is added in its entirety to the monomer phase. After dosing is complete, an initiator phase B, consisting of 0.021 parts ammonium persulfate and 2.909 parts water, is added and then the reaction mixture is post-polymerized for a further 4 hours at 90° C. before being cooled to <40° C.

Examples 2-13

The examples below (Table 1) are prepared analogously to Example 1. The crosslinking process stated in the table describes the type and time of the addition of the crosslinker. The letter "R" refers to an addition of the crosslinker into the reaction vessel, whereas the letter "M" describes an addition of the crosslinker into the monomer phase. The numbers indicate the time of the addition of the crosslinker in minutes after the start of the reaction (start of the monomer dosing). Example 13 was prepared like Example 1, except that the crosslinker was not added at a later time as an individual crosslinker phase, but weighed in the monomer phase with the other monomers and dosed in with the monomer phase within 30 minutes.

Abbreviations

MAA methacrylic acid
EA ethyl acrylate
A11/1800 polyglycol A11/1800 (Clariant)
Allylpolyalkylene glycol ether (EO 20 mol, PO 20 mol)
TMPTA trimethylolpropane triacrylate

TABLE 1

| | Examples 1-13 | | | | | | | | | | | | |
|---|---|---|---|---|---|---|---|---|---|---|---|---|---|
| Polymer | 1 | 2 | 3 | 4 | 5 | 6 | 7 | 8 | 9 | 10 | 11 | 12 | 13 |
| MAA | 37 | 37 | 37 | 37 | 45.4 | 45.4 | 45.4 | 45.4 | 45.4 | 50 | 45.4 | 45.4 | 37 |
| EA | 57.4 | 57.4 | 57.4 | 57.25 | 49 | 49 | 49.05 | 49 | 49 | 44.4 | 49 | 49.05 | 57.4 |
| A11/1800 | 5.4 | 5.4 | 5.4 | 5.4 | 5.4 | 5.4 | 5.4 | 5.4 | 5.4 | 5.4 | 5.4 | 5.4 | 5.4 |
| TMPTA | 0.3 | 0.3 | 0.3 | 0.45 | 0.3 | 0.3 | 0.15 | 0.2 | 0.2 | 0.2 | 0.2 | 0.15 | 0.30 |
| Crosslinking process | M20 | R30 | M25 | R30 | R20 | M20 | M20 | M20 | M15 | M20 | R20 | R20 | — |

TABLE 2

| Results Polymer Emulsions | | |
|---|---|---|
| Polymer | pH | Particle size* in mm |
| 1 | 2.55 | 86 |
| 2 | 2.53 | 87 |
| 3 | 2.49 | 84 |
| 4 | 2.63 | 90 |
| 5 | 2.51 | 99 |
| 6 | 2.55 | 99 |
| 7 | 2.49 | 95 |
| 8 | 2.59 | 94 |
| 9 | 2.63 | 93 |
| 10 | 2.53 | 104 |
| 11 | 2.53 | 96 |
| 12 | 2.50 | 93 |
| 13 | 2.50 | 89 |

*The particle size in the polymer emulsion is determined using dynamic light scattering (DLS) in a dilute aqueous sample of the emulsion at 25° C. ± 1° C.

Example 14

Unless stated otherwise, all quantitative data, fractions and percentages are based on the weight and the total amount or on the total weight of the preparation.

The polymer according to the invention is diluted with some of the water phase and added to the surfactant phase with stirring. The other formulation constituents apart from sodium hydroxide solution, citric acid and the suspended bodies are then added with stirring. After the pH has been adjusted to pH 5, the suspended bodies are stirred into the finished gel base with as little shearing as possible.

TABLE 3

Preparation Shower Gel

| | |
|---|---|
| Sodium laureth sulfate | 9.50 |
| Cocoamidopropylbetaine | 3.00 |
| Polymer | 2.25 |
| PEG-40 hydrogenated castor oil | 0.80 |
| PEG-7 glyceryl cocoate | 1.00 |
| Sodium benzoate | 0.45 |
| Sodium salicylate | 0.40 |
| Unispheres UEA-509 | 0.15 |
| Sodium hydroxide solution | ad pH 6.0 |
| Citric acid | ad pH 5.0 |

TABLE 3-continued

Preparation Shower Gel

| | |
|---|---|
| Perfume | 0.5 |
| Water | ad 100 |

TABLE 4

Results Preparation Shower Gel

| Polymer in the shower gel | tan δ | Viscosity in mPas | Turbidity in NTU |
|---|---|---|---|
| 1 | 0.24 | 3335 | 23 |
| 2 | 0.39 | 3057 | 7 |
| 3 | 1.00 | 3001 | 14 |
| 4 | 1.22 | 2761 | 10 |
| 5 | 0.12 | 3413 | 25 |
| 6 | 0.17 | 3021 | 26 |
| 7 | 0.24 | 2906 | 14 |
| 8 | 0.17 | 3525 | 19 |
| 9 | 0.11 | 4169 | 25 |
| 10 | 0.22 | 3089 | 23 |
| 11 | 0.12 | 2903 | 22 |
| 12 | 0.18 | 2825 | 18 |
| 13 | 0.07 | 5785 | 80 |

The viscosity of the preparations is measured on a rheometer at 25° C.±1° C. with 40 mm cone/plate geometry (1° cone angle) with a gap of 0.03 mm, charging being carried out in a structure-preserving manner. A suitable constant shear rate time ramp of 0.1-1000 $s^{-1}$ is predefined and a corresponding structure recovery time is observed before the test. The viscosity is given for a shear rate of 10 $s^{-1}$.

Preparation 13, prepared with the polymer according to Example 13, has an excessively high viscosity and undesired severe turbidity. Moreover, it has a high yield point, which is manifested in a very low tan δ. The high yield point leads to the preparation no longer being flowable and consequently it is unable to flow by itself out of a bottle. Preparations 1-12 do not have this disadvantage.

Example 15

Certain polymers such as Carbopol® AQUA SF-2 (Lubrizol) exhibit increasing turbidity at higher temperatures. This is undesired especially in countries with relatively high daytime temperatures or generally in the summer months, and may be interpreted by the consumer as defective product quality.

A preparation as shown in Table 3 with Carbopol® AQUA SF-2 and the polymer from Example 8 was prepared and compared.

TABLE 5

Turbidity values compared to AQUA SF-2

| | 22° C. | 30° C. | 35° C. | 40° C. | 50° C. | 22° C. | 22° C. after 72 h | 22° C. 1 week |
|---|---|---|---|---|---|---|---|---|
| Example 8 | 18 | 19 | 18 | 18 | 18 | 19 | 18 | 18 |
| Aqua SF-2 | 24 | 24 | 26 | 37 | 140 | 31 | 27 | 26 |

The polymers according to the invention do not have temperature-dependent turbidity, whereas the Carbopol® AQUA SF-2 becomes more and more turbid with increasing temperature.

What is claimed is:

1. A polymer, wherein the polymer is obtainable by radical emulsion polymerization of
   (A) at least one acidic vinyl monomer or salt thereof,
   (B) at least one nonionic vinyl monomer,
   (C) at least one monomer containing an unsaturated end group and a polyoxyalkylene moiety,
   (D) at least one crosslinking monomer,
   (E) optionally, a protective colloid,
   the polymerization being controlled such that
   (F) at least at times the gel effect occurs, achieved by adding monomers (A), (B) and (C) within 120 minutes, and
   (G) the crosslinking monomer (D) is added at the earliest 10 minutes after a first addition of monomers (A), (B) and (C).

2. The polymer of claim 1, wherein (B) comprises a hydrophobic nonionic vinyl monomer.

3. The polymer of claim 1, wherein no associative monomers are present.

4. The polymer of claim 1, wherein (A) comprises at least one of methacrylic acid, an alkali metal salt thereof, an alkaline earth metal salt thereof, an ammonium salt thereof, and an alkylammonium salt thereof.

5. The polymer of claim 1, wherein (B) comprises at least one monomer selected from C1-C22-alkyl acrylates and C1-C22-alkyl methacrylates.

6. The polymer of claim 1, wherein (C) comprises at least one monomer selected from vinylpolyalkylene glycols and polymerizable surfactants.

7. The polymer of claim 1, wherein (C) comprises at least one monomer selected from ethoxylated and propoxylated 1,4-butanediol vinyl ether having 30 ethyleneoxy and propyleneoxy units, allylpolyethylene glycol ethers having 30 ethyleneoxy units, allylpolyethylene glycol ethers having 20 ethyleneoxy units, vinylpolyethylene glycol ethers having 20 ethyleneoxy units, $CH_2=CHCH_2O[(CH_2CH_2O)_n(CH_2(CH_3)CHO)]_mCH_3$ where m+n=5 to 100 and n/m=1, and polyalkylene glycol allyl butyl ethers having 25 ethyleneoxy and 8 propyleneoxy units.

8. The polymer of claim 1, wherein (D) comprises at least one monomer selected from polyol (meth)acrylates having at least two (meth)acrylate groups and mixed esters of polyols with acrylic acid and/or methacrylic acid.

9. The polymer of claim 1, wherein the polymer comprises from 10% to 75% of (A), from 10% to 90% of (B), from 0.5% to 40% of (C), and up to 1% of (D).

10. The polymer of claim 1, wherein the polymer comprises from 20% to 60% of (A), from 40% to 80% of (B), from 1% to 10% of (C), and from 0.05% to 0.5% of (D).

11. The polymer of claim 1, wherein a mass ratio (A):(B) is from 1:2.2 to 1.5:1.

12. A polymer, wherein the polymer is obtainable by radical emulsion polymerization of
(A) at least one acidic vinyl monomer or salt thereof,
(B) at least one nonionic vinyl monomer,
(C) at least one monomer containing an unsaturated end group and a polyoxyalkylene moiety,
(D) at least one crosslinking monomer,
(E) optionally, a protective colloid,
the polymerization being controlled such that
(F) at least at times the gel effect occurs, achieved by adding monomers (A), (B) and (C) within 60 minutes and
(G) the crosslinking monomer (D) is added at the earliest 15 minutes after a first addition of monomers (A), (B) and (C),
and wherein (A) comprises at least one of methacrylic acid, an alkali metal salt thereof, an alkaline earth metal salt thereof, an ammonium salt thereof, and an alkylammonium salt thereof, (B) comprises at least one monomer selected from C1-C22-alkyl acrylates and C1-C22-alkyl methacrylates, (C) comprises at least one monomer selected from ethoxylated and propoxylated 1,4-butanediol vinyl ether having 30 ethyleneoxy and propyleneoxy units, allylpolyethylene glycol ethers having 30 ethyleneoxy units, allylpolyethylene glycol ethers having 20 ethyleneoxy units, vinylpolyethylene glycol ethers having 20 ethyleneoxy units, $CH_2=CHCH_2O[(CH_2CH_2O)_n(CH_2(CH_3)CHO)]_mCH_3$ where m+n=5 to 100 and n/m=1, and polyalkylene glycol allyl butyl ethers having 25 ethyleneoxy and 8 propyleneoxy units, and (D) comprises at least one monomer selected from polyol (meth)acrylates having at least two (meth)acrylate groups and mixed esters of polyols with acrylic acid and/or methacrylic acid.

13. The polymer of claim 12, wherein the polymer comprises from 28% to 52% of (A), from 40% to 62% of (B), from 2% to 6% of (C), and from 0.1% to 0.3% of (D).

14. A thickened preparation, wherein the preparation comprises the polymer of claim 1.

15. The preparation of claim 14, wherein the preparation is aqueous and comprises from 0.5% to 5% of the polymer.

16. The preparation of claim 1, wherein (A) consists of methacrylic acid, (B) consists of ethylacrylate and (C) consists of allylpolyalkylene glycol ether having 20 ethyleneoxy units and 20 propyleneoxy units.

17. The preparation of claim 16, wherein D consists of trimethylolpropane triacrylate.

18. The polymer of claim 17, wherein the polymer comprises from 28% to 52% of (A), from 40% to 62% of (B), from 2% to 6% of (C), and from 0.1% to 0.3% of (D).

19. The preparation of claim 1, wherein monomers (A), (B) and (C) are added within 60 minutes.

20. The preparation of claim 1, wherein monomer (D) is added at the earliest 15 minutes after the first addition of monomers (A), (B) and (C).

* * * * *